(12) United States Patent
Mitrani

(10) Patent No.: US 7,297,540 B2
(45) Date of Patent: Nov. 20, 2007

(54) METHODS OF GENERATING TISSUE USING DEVITALIZED, ACELLULAR SCAFFOLD MATRICES DERIVED FROM MICRO-ORGANS

(75) Inventor: Eduardo N. Mitrani, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 748 days.

(21) Appl. No.: 10/045,018

(22) Filed: Jan. 15, 2002

(65) Prior Publication Data

US 2003/0148510 A1    Aug. 7, 2003

(51) Int. Cl.
*C12N 5/00*    (2006.01)
*C12N 5/02*    (2006.01)
*A01N 1/00*    (2006.01)
*A01N 1/02*    (2006.01)
*A01N 63/00*   (2006.01)

(52) U.S. Cl. .................. 435/395; 435/325; 435/1.1; 424/93.1; 424/93.21; 424/93.2

(58) Field of Classification Search .............. 435/1.1
See application file for complete search history.

(56) References Cited

U.S. PATENT DOCUMENTS

| | | | | |
|---|---|---|---|---|
| 5,266,480 A | * | 11/1993 | Naughton et al. | ........... 435/371 |
| 5,770,417 A | * | 6/1998 | Vacanti et al. | ............... 435/180 |
| 5,855,610 A | * | 1/1999 | Vacanti et al. | ............. 632/2.13 |
| 5,861,313 A | | 1/1999 | Pang et al. | |
| 5,888,720 A | | 3/1999 | Mitrani | |
| 6,197,575 B1 | | 3/2001 | Griffith et al. | |
| 6,326,201 B1 | | 12/2001 | Fung et al. | |
| 2002/0115208 A1 | * | 8/2002 | Mittchell et al. | ........... 435/325 |

FOREIGN PATENT DOCUMENTS

| WO | 01/00859 | 1/2001 |
|---|---|---|
| WO | 01/07098 | 2/2001 |

OTHER PUBLICATIONS

Riviere, 1995, PNAS, vol. 97, pp. 6733-6737.*
Schumacher, 2001, Jour Biol. Chem., vol. 276, pp. 7337-7345.*
Liu, 2003, Jour Cell Biochem, vol. 88, pp. 29-40.*

* cited by examiner

*Primary Examiner*—Scott D. Priebe
*Assistant Examiner*—Valarie Bertoglio

(57) ABSTRACT

Methods of generating, and isolating adult stem cells and utilizing such cells and/or embryonic stem cells in generating tissue of a specific function and micro-architecture are provided.

10 Claims, 4 Drawing Sheets
(4 of 4 Drawing Sheet(s) Filed in Color)

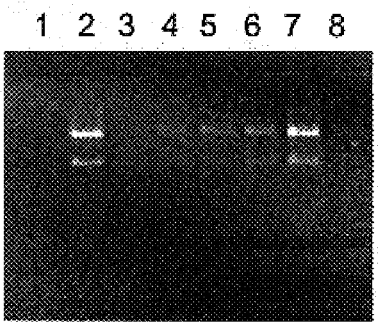 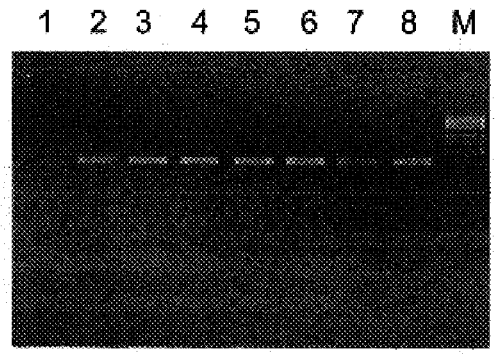
Fig. 4              Fig. 5
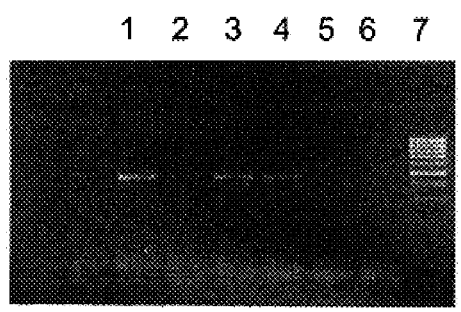 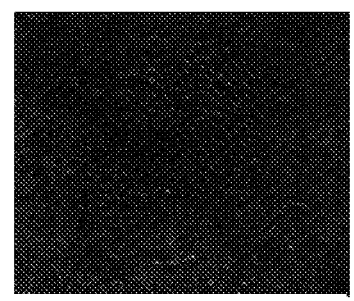
Fig. 6              Fig. 7
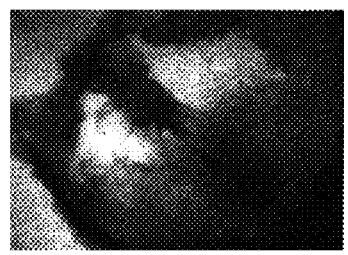 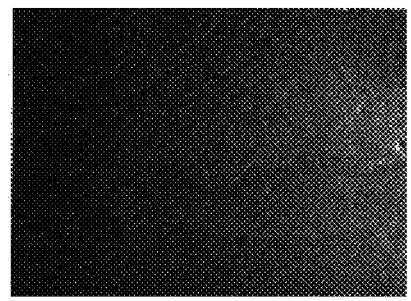
Fig. 8              Fig. 9

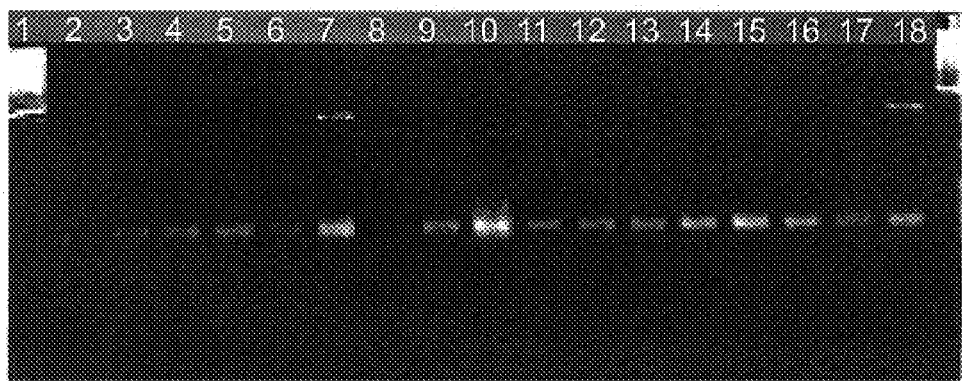
Fig. 16
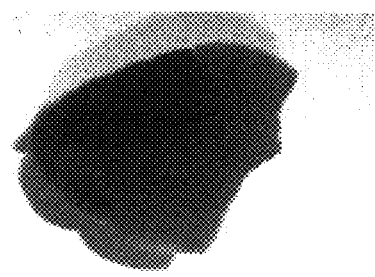 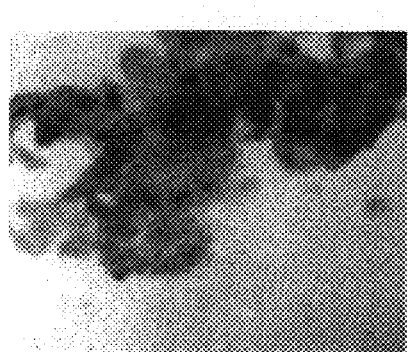
Fig. 17a     Fig. 17b

SEQUENCE LISTING

```
<160> NUMBER OF SEQ ID NOS: 18

<210> SEQ ID NO 1
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1
taccacaggc attgtgatgg                                              20

<210> SEQ ID NO 2
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2
aatagtgatg acctggccgt                                              20

<210> SEQ ID NO 3
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 3
cgagccatcc gactggagc                                               19

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 4
gactcggact caggtgaggt                                              20
```

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5
acaccatcgc tacctttcc                                               20

<210> SEQ ID NO 6
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 6 ctttcctta cagacttcca cc                                            22

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
tcatgctgtc catctgctgc                                              20

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
aaagaggaag gagggttcg                                               20

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
cgaagatggt caagtcgtac                                              20

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
ggcaaaccag ttgtagacac                                              20

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
ttcagtcaac agaaccaggg                                           20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
ctctgtgcaa tggccatgac                                           20

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
gattgacaac ctgctgcagg                                           20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
cctgcagcag gttgtcaatc                                           20

<210> SEQ ID NO 15
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 15
gagagagcta tcatcatgtc c                                         21

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
gtcaggatag aagacaggat                                           20

<210> SEQ ID NO 17
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 17
tcacactgag tggaggtca                                            19

<210> SEQ ID NO 18

-continued

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18 ggagtcttt gcacaatgga                                              20
```

METHODS OF GENERATING TISSUE USING DEVITALIZED, ACELLULAR SCAFFOLD MATRICES DERIVED FROM MICRO-ORGANS

FIELD AND BACKGROUND OF THE INVENTION

The present invention relates to methods of generating tissue using scaffold matrices derived from micro-organs and stem cells of embryonic or adult origin. The present invention further relates to novel approaches for inducing differentiation of adult or embryonic stem cells for isolating adult stem cells and a method of continuously generating stem cells by implantation of micro-organs as sources of stem cells.

Stem Cells (SCs)

Until very recently it was believed that only certain embryonic cells retain the capacity or competence of being able to differentiate into most, if not all, of the cell types that constitute the vertebrate body (pluripotent stem cells). With the advent of bone marrow transplantation and other remarkable experiments it is now clear that also in the vertebrate adult including man there exists in tissues like bone marrow, adipose tissue and brain, true stem cells with the capacity or competence to differentiate into many other cell types, in a process generally referred to as transdifferentiation, if provided with the appropriate stimuli (Bjorson et al 1999, Mezey et al 2000, Orlic et al 2001, Kocher et al 200). Prior to the publication of these remarkable experiments, it was believed that there existed stem cells in some adult tissues like gut and skin, but that the differentiation potential of these stem cells in adult tissues is limited to cell lineages present in the organ from which they were derived.

Recent studies have shown that certain stem cells in adult tissue express more of a "pluripotent character" than previously thought. Bone marrow (BM) cells were shown to differentiate into various cell types, including liver. Neural stem cells were recently shown to be capable of repopulating the hematopoietic system, producing blood cells and integrating and differentiating into various other tissue types. Other examples are also known. In these examples "real" stem cells (SCs) were used, in the sense that they can give rise to cells from organs different than the organ of origin. In most of these examples, the SC derived from any of the three germ layers, the ectoderm, the mesoderm or the endoderm have been shown to differentiate into cells whose phenotype corresponds to a different germ layer, e.g., ectoderm into mesoderm, etc.

Clearly then, SCs exist both in early embryos and in adult tissues. While SCs are now known to have a competence to differentiate along various lineages, the following goals still await further developments (i) to find protocols with which to induce SCs differentiation along a differentiation lineage of choice; and (ii) once differentiated, to incorporate SCs into organized complex three-dimensional structures or tissues that constitutes the vertebrate body.

The present invention offers general and applicable solutions to these two goals.

Embryonic Stem Cells

Embryonic stem (ES) cells (ESCs) have commonly been derived from pre-implantation embryos. When cultured under proper conditions (fibroblast feeder layer or the addition of Leukemia inhibitory factor (LIF)) ESCs maintain both the ability to multiply in culture and their totipotential capacity (Keller, 1995). In this aspects as well as in their gene expression pattern, ESCs resemble the inner cell mass (ICM) of the developing embryo (O'Shea, 1999). The following examples provide insight with respect to the differentiation potential of ESCs:

(i) When injected into the ICM of a blastocyst, ESCs integrate into the ICM and populate all cell lineages including the germ line.

(ii) When injected subcutaneously into syngeneic mice, teratocarcinoma tumors, which contain cells of different embryonic origins develop (Rudnicki and McBurney, 1987).

(iii) When cultured in vitro, ESCs aggregate and generate colonies known as embryoid bodies (EB) (Keller, 1995). Overexpression of hepatocyte nuclear factor 3 (HNF3) was shown to promote ESCs' differentiation into endodermal lineage in vitro (Levinson-Dushnik and Benvenisty, 1997).

Adult Stem Cells

It was originally thought that only ESCs are totipotent. The differentiation potential of SCs in adult tissue was thought to be limited to cell lineages present in the organ from which they were derived. Recent studies have shown that certain stem cells in adult tissue express more of a "pluripotent character" than previously thought. For instance, bone marrow (BM) cells were shown to differentiate into various cell types, including liver cells. Hematopoetic SCs were recently shown to be capable of differentiating into neurons (Mezey et al 2000; Recently Kocher et al. (2001) have reported neovascularization of ischemic myocardium of athymic nude rats by cytokine-mobilized human bone-marrow-derived stem cells (Kocher et al 2001). In such experiments, as well as in the experiments reported by Orlic et al. (2001), homing of the stem cells was attributed to the acute injury inflicted by the experimental procedure.

Micro Organs (MOs)

Micro organs are organ portions of unique characters. On the one hand, MOs are of sufficient size so as to preserve the micro-architecture of the tissue or organ from which they were derived. On the other hand, they are of dimensions which allow efficient nutrients and wastes exchange by diffusion with the growth medium in which they are kept. As such, MOs retain viability in culture for as long as 45 days or more, and they were shown to transcribe tissue specific genes throughout this time period. Furthermore, since cell interactions are kept and different cell types of the MO are cultured together, MOs can be cultured in serum-free media. The development of the MOs technology which is further described in U.S. Pat. No. 5,888,720, and PCT Applications No. IL00/00365, IL00/00424 and US98/00594, all of which are incorporated herein by reference, was following the observation that every tissue in the body of a multi-cellular organism having a blood system is composed of tissue units, each such unit is composed of numerous cell types, each of which is positioned not more than 225–300 μm away from a nearest blood vessel, which distance is, in effect, dictated by diffusion rates of nutrients and wastes. This observation was translated, as described in the above Patent and Applications, into the MOs technology, according to which an MO is prepared from a tissue so as to include all the cell types of a tissue unit, each of which is positioned not more than 225–300 μm away from a growth medium in which the MO is placed, which distance allows efficient diffusion rates of nutrients and wastes, so as to sustain MO viability in minimal (serum free) medium for long time periods.

There is thus a highly recognized need for, and it would be highly advantageous to have methods of generating adult stem cells and methods of utilizing adult and embryonic stem cells for generating differentiated and functional tissues.

SUMMARY OF THE INVENTION

The present invention serves three purposes: (i) to use micro-organs as a (continuous) source of adult stem cells; (ii) to use the natural multi-signaling micro-environment of micro-organs to induce differentiation in stem cells; and (iii) to use the natural three-dimensional structure of an MOs acellular matrix as a scaffold for seeding stem cells of adult or embryonic origin.

According to another aspect of the present invention there is provided a method of generating adult stem cells comprising implanting at least one micro-organ derived from adult tissue in a mammal in a manner enabling migration of cells out of the at least one micro-organ, the cells being adult stem cells.

According to further features in preferred embodiments of the invention described below, the method further comprising isolating the adult stem cells migrating out of the at least one micro-organ According to still further features in the described preferred embodiments the adult stem cells are isolated from a biological fluid collected from the mammal.

According to another aspect of the present invention there is provided a method of isolating adult stem cells comprising culturing at least one micro-organ derived from an adult tissue in a culture and isolating cells migrating out of the at least one micro-organ, the cells being adult stem cells.

According to still further features in the described preferred embodiments the culturing is effected under conditions suitable for maintaining the cells migrating out of the at least one micro-organ in an undifferentiated state.

According to still further features in the described preferred embodiments the culturing is effected under conditions suitable for propagation of the cells migrating out of the at least one micro-organ.

According to another aspect of the present invention there is provided a method of inducing stem cells differentiation, the method comprising co-culturing isolated stem cells and at least one micro-organ, thereby inducing stem cells differentiation.

According to yet another aspect of the present invention there is provided a method of inducing stem cells differentiation, the method comprising culturing isolated stem cells in micro-organ conditioned medium, thereby inducing stem cells differentiation.

According to still another aspect of the present invention there is provided a method of generating an artificial micro-organ comprising: (a) providing an acellular three dimensional scaffold, the acellular three dimensional scaffold being of dimensions selected such that when populated with cells, the cells positioned deepest within the scaffold are at least about 100 micrometers and not more than about 225 micrometers away from the cells positioned at a nearest surface formed on the scaffold; and (b) seeding the acellular three dimensional scaffold with cells at least until the cells repopulate the acellular three dimensional scaffold.

According to still further features in the described preferred embodiments the method further comprising the step of generating the acellular three dimensional scaffold from a micro-organ.

According to still further features in the described preferred embodiments the step of generating is effected by subjecting the micro-organ to conditions selected suitable for removing cells and not acellular matrix from the micro-organ.

According to still further features in the described preferred embodiments the cells seeded on the acellular three dimensional scaffold are stem cells.

According to still further features in the described preferred embodiments the stem cells are adult stem cells.

According to still further features in the described preferred embodiments the stem cells are embryonic stem cells.

According to still further features in the described preferred embodiments the cells seeded on the acellular three dimensional scaffold are a mixed population of cells including stem cells and differentiated cells.

According to still further features in the described preferred embodiments the cells seeded on the acellular three dimensional scaffold are genetically transformed to express at least one exogenous polypeptide.

According to still further features in the described preferred embodiments the stem cells are genetically transformed to express at least one exogenous polypeptide.

According to still further features in the described preferred embodiments the micro-organ is derived from an adult tissue of a type selected from the group consisting of skin, kidney, liver, gut derived tissue and bone marrow.

The present invention successfully addresses the shortcomings of the presently known configurations by providing novel approaches for isolating adult stem cells, for differentiating and using stem cells of an adult or embryonic origin to generate organized three dimensional micro-organ like structures.

BRIEF DESCRIPTION OF THE DRAWINGS

The file of this patent contains at least one drawing executed in color. Copies of this patent with color drawings will be provided by the Patent and Trademark Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1:
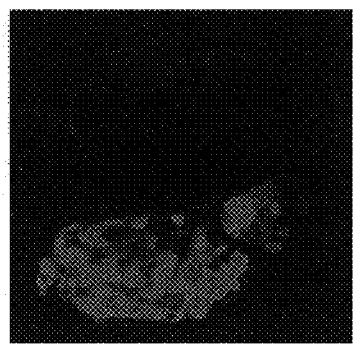

FIG. 1 is a fluorescence microscope image of embryoid bodies (at concentrations between 50000–250000 cells/ml) co-cultured with lung derived mouse micro organs for 6 days, demonstrating the micro organs' ability to sustain growth of embryoid bodies. Embryoid body cells express the green fluorescent protein GFP5 and thus can be distinguished under an UV microscope emitting blue light as exciter. Note that cells remain viable and adhere to the micro organs.

Figure 2A:
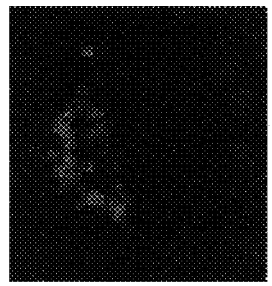
Figure 2B:

FIGS. 2a–b are GFP fluorescent (FIG. 2a) and standard hematoxylin and eosin (FIG. 2b) stained microscope images of embryoid bodies (at concentrations between 50,000–250,000 cells/ml) co-cultured with lung derived mouse micro organs for 17 days, demonstrating arrangement of the embryoid bodies into alveoli-type structures.

Figure 3:

FIG. 3 is a standard hematoxylin and eosin stained high magnification microscope image of embryoid bodies (at concentrations between 50,000–250,000 cells/ml) co-cultured with lung derived mouse micro organs for 17 days, demonstrating arrangement of the embryoid bodies into alveoli-type structures.

FIG. 4 is a photograph of an ethidium bromide stained agarose gel demonstrating that micro organ endogenous cells can be selectively killed by neomycin while transduced, neomycin-resistant mouse embryonic stem cells survive within the micro organ structures, as determined by transcription of ribosomal RNA. Lane 1=RNA from lung MOs, Lane 2=RNA from lung MOs and embryonic stem cells, Lane 3=RNA from lung MOs and embryonic stem cells, Lane 4=RNA from lung MOs and embryonic stem cells (1:5), Lane 5=lung MOs and trypsinized embryoid bodies (as cell suspension), Lane 6=RNA from lung MOs and trypsinized embryoid bodies (diluted 1:5), Lane 7=RNA from embryoid bodies alone, Lane 8=RNA from embryonic stem cells alone. Trypsinized embryoid bodies are embryoid bodies that underwent trypsinization into single cells before co-culturing with MOs. Cultures were maintained for 21 days in the presence of 250 μg/ml neomycin after which RNA was extracted and analyzed.

FIG. 5 is a photograph of an ethidium bromide stained agarose gel demonstrating RT-PCR evidence of housekeeping gene (actin) transcription in the transformed, neomycin-resistant mouse embryonic cells, but not in the mouse micro organs. The actin gene is not transcribed in mouse lung derived MOs when cultured in the presence of neomycin, indicating that MO cells are killed in the presence of neomycin (lane 1). In lung mouse MOs co-cultured with neomycin-resistant embryonic stem cells or embryoid bodies, the embryonic cells replaced the MO original cells and transcribe the actin gene (lanes 2–6). Lane 1=lung MOs, Lane 2=lung MOs and embryonic stem cells, lane 3=lung MOs and embryonic stem cells, lane 4=lung MOs and embryonic stem cells (embryonic stem cells at a 5-fold lower concentration), lane 5=lung MOs and trypsinized embryoid body cells, lane 6=lung MOs and trypsinized embryoid body cells (1:5), lane 7=embryoid bodies alone, lane 8=embryonic stem cells alone. Cultures were maintained for 21 days in the presence of 250 μg/ml neomycin after which RNA was extracted and analyzed by RT-PCR.

FIG. 6 is a photograph of an ethidium bromide stained agarose gel demonstrating induction of differentiation in embryonic cells (at concentrations between 25,000–150,000 cells/ml) co-cultured with micro organs, and RT-PCR detection of surfactant protein-C (a specific lung cell marker) expression. Neomycin-resistant mouse embryonic stem cells or embryoid bodies were incorporated into mouse lung derived MOs. In both cases co-culture with MOs induced expression of the lung specific marker of differentiation, the surfactant protein-C gene, in the embryonic cells. Lane 1=lung MOs, lane 2=lung MOs and embryonic stem cells, lane 3=lung MOs and embryonic stem cells, lane 4=lung MOs and embryonic stem cells (embryonic stem cells at a 5-fold lower concentration), lane 5=lung MOs and trypsinized embryoid body cells, lane 6=lung MOs and trypsinized embryoid body cells (diluted 1:5), lane 7=embryoid bodies alone, lane 8=embryonic stem cells alone. Cultures were maintained for 21 days in the presence of 250 μg/ml neomycin, after which RNA was extracted and analyzed by RT PCR as is further described in the Examples section that follows.

FIG. 7 is a phase contrast micrograph of a colony of β-galactosidase transgenic mouse skin derived adult stem cells originating from micro organs grown on a feeder layer of STO cells. The feeder layer was prepared as described in the Material and Methods section, and replated twice on fresh STO cell feeder layers until they proliferated enough to cover the whole layer.

FIG. 8 is a photograph demonstrating the integration of cultured, mouse skin micro organ derived adult stem cells (between 600–3,000 cells/embryo) into early chick embryos. The photograph is a top view of x-gal staining of a stage 3 chick embryo grown in agar for three days following injection of MO-derived β-galactosidase transgenic skin adult stem cells on day 0 (between 600–3,000 cells/embryo). The proliferation of blue stained putative skin cells is apparent mainly in the extra-embryonic peripheral regions.

FIG. 9 is a photograph depicting the tissue-specific integration of mouse micro organ derived skin putative adult stem cells into the neural plate of a stage 3 chick embryo. Following injection of (between 600–3,000 cells/embryo) cultured, MO-derived β-galactosidase transgenic skin adult stem cells, chick embryos were grown in agar for 24 hrs until they reached the neurula stage, sectioned, fixed and exposed to X-gal as described to visualize the location of blue-staining MO derived putative skin stem cells. In this representative section the blue-staining skin putative adult stem cells can be seen integrated into the neural tube and endoderm.

Figure 10:
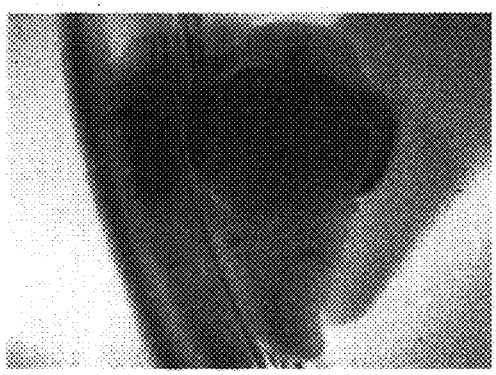

FIG. 10 is a photograph depicting the tissue-specific integration of mouse micro organ derived skin putative adult stem cells into brain structures of late stage chick embryos. Following injection of (between 600–3,000 cells/embryo) cultured, MO-derived β-galactosidase transgenic skin adult stem cells, into stage 18 chick embryos in ovo, the embryos were incubated for an additional 3 days, fixed and exposed to X-gal as described to visualize the location of blue-staining MO derived putative skin cells. In this top view of an embryo grown for an additional three days the blue-staining MO derived skin putative adult stem cells can be seen inside regions of the mid and hind brain.

Figure 11:
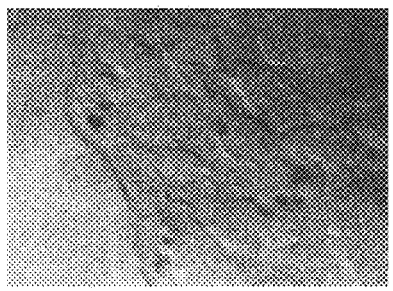

FIG. 11 is a photograph depicting the integration and differentiation of β-galactosidase transgenic skin adult stem cells into lung micro organs. Mouse skin putative adult stem were co-cultured with rat lung micro-organs cells (at concentrations between 0.1 and 0.5 million cells/ml) for a period of 10 days after which the cultures were fixed and processed for standard histology and stained with x-gal for visualization of the blue-staining adult stem cells. Note the blue-staining adult stem cells organizing as part of distinct alveolar structures.

Figure 12:

FIG. 12 is a photograph demonstrating viability of and stem cells extruded from a mouse Bone Marrow micro organ derived from Roza transgenic mouse, maintained in a syngeneic host. The β-galactosidase transgenic bone marrow micro organs (gray arrow) were prepared as described above, implanted subcutaneously into a syngeneic (non-transgenic, β-galactosidase negative) mouse and maintained for two weeks. In the photograph, viability, integrity and vascularization of the MO are evident. In addition, expression of the β-galactosidase gene, indicating transgenic bone marrow origin, is apparent in cells a distance (black arrow) from the MO, demonstrating the ability of micro organs to release stem cells into surrounding tissue.

Figure 13:

FIG. 13 is a photograph demonstrating the ability of de-vitalized micro organ three-dimensional scaffolds to support proliferation of mouse Bone Marrow stem cells. Devitalized rat liver micro organ scaffolds prepared as described above were plated with bone marrow stem cells (between 1,000–5,000 cells/MO) derived from β-galactosidase transgenic mice, grown for 9 days, fixed and stained with x-gal for indication of bone marrow origin. In this whole view, the blue-staining β-galactosidase positive cells can be seen adhering to the devitalized liver micro organ scaffold.

Figure 14:

FIG. 14 is a photograph of a transverse section depicting the proliferation of β-galactosidase transgenic bone marrow stem cells (at concentrations between 10,000–100,000 cells/ml) supported by devitalized lung micro organ three-dimensional scaffolds. Rat lung devitalized MO scaffolds were prepared as described above, plated with β-galactosidase transgenic derived mouse bone marrow stem cells, grown for 9 days, sectioned, fixed and stained with x-gal for detection of β-galactosidase positive cells. The blue-staining bone marrow cells can be seen adhering to the scaffold. Induction of differentiation by the devitalized scaffold is indicated by the preservation of lung alveolar structure despite the β-galactosidase transgenic bone marrow origin of the cells lining the alveolar cavities (blue-staining, expressing β-galactosidase).

Figure 15:
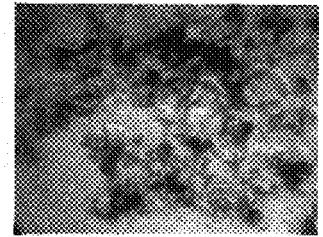

FIG. 15 is a photograph demonstrating proliferation and differentiation of β-galactosidase transgenic bone marrow stem cells (at concentrations between 10,000–100,000 cells/ml) in devitalized lung micro organ three-dimensional scaffolds. Devitalized rat lung micro organ scaffolds prepared as described above were plated and grown for 9 days with β-galactosidase transgenic-derived mouse bone marrow stem cells, fixed, sectioned and stained with x-gal for detection of β-galactosidase positive cells of bone marrow origin. The blue staining bone marrow cells can be seen adhering to the scaffold. Induction of differentiation by the devitalized scaffold is indicated by the preservation of lung alveolar structure despite the transgenic bone marrow origin of the cells lining the alveolar cavities (blue-staining, expressing β-galactosidase).

FIG. 16 is a photograph of an ethidium bromide stained 2% agarose gel demonstrating the differentiation of β-galactosidase transgenic bone marrow stem cells (at concentrations between 10,000–100,000 cells/ml) in devitalized lung micro organ three-dimensional scaffolds. Devitalized rat lung micro organ scaffolds prepared as described above were plated and grown for 9 days with β-galactosidase transgenic-derived mouse bone marrow stem cells. Total RNA was prepared as described in the Materials and Methods section that follows, cDNA prepared by reverse transcription, and used to detect tissue specific genes by RT-PCR. On the gel: lanes 1 and 19 are DNA size markers, lane 2 and 3 are RNA from rat lung micro organ scaffolds prepared as described above and maintained in the absence of added bone marrow stem cells. As expected, no expression of CC-10—a clara cell lung specific gene—was observed in these cells. In contrast, in two experiments in which devitalized rat lung micro organ scaffolds prepared as described above were maintained in the presence of bone marrow stem cells (lanes 7 and 18), the latter differentiated into lung cells as indicated by the presence of CC-10 transcripts. Differentiation of bone marrow derived stem cells into lung cells was not observed in all experimental conditions: in others (for example, lanes 4–6 and 8–17) no expression of CC-10 was detected.

FIGS. 17a–b are photographs demonstrating the proliferation, migration and differentiation of stem cells from transgenic Roza mouse Bone Marrow micro organs, maintained in regenerating syngeneic mouse liver. Five β-galactosidase transgenic bone marrow micro organs, prepared as described above, were implanted on an absorbable hemostatic matrix (Spongiostan, Johnson and Johnson) over the exposed liver tissue of a partially hepatectomized syngeneic (non-transgenic, β-galactosidase negative) mouse. Ten days later the animals were sacrificed, the implanted region stained with x-gal and sectioned for histological analysis. In the photograph of whole mounted implanted matrix (FIG. 17a), the migration of blue-staining cells, indicating MO transgenic bone marrow origin, is apparent over the entire matrix surface. In the micrograph of the fixed and sectioned stained matrix (FIG. 17b), transgenic (blue staining) MO derived cells are clearly incorporated into newly forming liver sinusoids.

DESCRIPTION OF THE PREFERRED EMBODIMENTS

The present invention is of methodology which can be used to isolate adult stem cells, differentiate such stem cells as well as embryonic stem cells into functional tissue and generate synthetic micro-organ structures using stem cells and micro-organ scaffolds.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

For purposes of this specification and the accompanying claims, the terms "micro-organs", "MC", and "MCs" refer to at least one, preferably a plurality of, explants of tissue which retain the basic cell-cell, cell-matrix and cell-stroma architecture of the originating tissue. These terms refer to isolated as well as cultured explants. Additionally, these terms refer to explants co-cultured with cells derived from a suspension, and to planar organs formed by co-culture of explants and a plurality of individual cells.

Since the dimensions of the explant are important to the viability of the cells therein, if micro-organ functionality is intended to be sustained for prolonged periods of time (in-vivo, e.g., implanted or ex-vivo, e.g., cultured), such as 1–21 days or longer, the dimensions of the tissue explant are selected to provide diffusion of adequate nutrients and gases such as oxygen to every cell in the three dimensional micro-organ, as well as diffusion of cellular waste out of the explant so as to minimize cellular toxicity and concomitant death due to localization of the waste in the micro-organ. Accordingly, the size of the explant is determined by the requirement for a minimum level of accessibility to each cell in the absence specialized delivery structures or synthetic substrates. It has been previously discovered that this accessibility can be maintained if the surface to volume index falls within a certain range.

This selected range of surface area to volume index provides the cells sufficient access to nutrients and to avenues of waste disposal by diffusion according to existing biological diffusion limits as can be realized by considering the maximum volume to surface area that a developing mammalian embryo can reach before circulation sets in and cells survive by diffusion. These biological diffusion limits can also be realized by noticing that in mammalian epithelium-containing tissues, almost without exception, no cell is approximately more than 200 micrometers from a blood capillary vessel.

This level of accessibility can be attained and maintained if the surface area to volume index, defined herein as "Aleph" or "Aleph index", is at least about 2.6 mm$^{-1}$. The third dimension has been ignored in determining the surface area to volume index because variation in the third dimension causes ratiometric variation in both volume and surface area. However, when determining Aleph, a and x should be defined as the two smallest dimensions of the tissue slice.

For purposes of this specification and the accompanying claims, "Aleph" refers to a surface area to volume index given by a formula 1/x+1/a, wherein x=tissue thickness and a=width of tissue in mm. In preferred embodiments, the Aleph of an explant is in the range of from about 2.7 mm$^{-1}$ to about 25 mm$^{-1}$, more preferably in the range of from about 2.7 mm$^{-1}$ to about 15 mm$^{-1}$, and even more preferably in the range of from about 2.7 mm$^{-1}$ to about 10 mm$^{-1}$. Examples of Aleph are provided in Table 1 wherein, for example, a tissue having a thickness (x) of 0.1 mm and a width (a) of 1 mm would have an Aleph index of 11 mm$^{-1}$.

Thus, for example, cells positioned deepest within an individual micro-organ culture or explant are at least about 100 micrometers and not more than about 225 micrometers away from a nearest surface of the individual micro-organ culture, thereby in vivo architecture is preserved while at the same time it is ensured that no cell is farther than about 225 micrometers from the source of gases and nutrients.

TABLE 1

Different values for the surface area to volume ratio index "Aleph", as a function of a (width) and x (thickness) in mm$^{-1}$

| | Values of Aleph | | | | |
|---|---|---|---|---|---|
| x (mm) | a = 1 | a = 2 | a = 3 | a = 4 | a = 5 |
| 0.1 | 11 | 10.51 | 10.33 | 10.2 | 10.2 |
| 0.2 | 6 | 5.5 | 5.33 | 5.25 | 5.2 |
| 0.3 | 4.3 | 3.83 | 3.67 | 3.58 | 3.53 |
| 0.4 | 3.5 | 3 | 2.83 | 2.75 | 2.7 |
| 0.5 | 3 | 2.5 | 2.33 | 2.25 | 2.2 |
| 0.6 | 2.66 | 2.16 | 2 | 1.91 | 1.87 |
| 0.7 | 2.4 | 1.92 | 1.76 | 1.68 | 1.63 |
| 0.8 | 2.25 | 1.75 | 1.58 | 1.5 | 1.45 |
| 0.9 | 2.11 | 1.61 | 1.44 | 1.36 | 1.31 |
| 1.0 | 2 | 1.5 | 1.33 | 1.25 | 1.2 |
| 1.2 | 1.83 | 1.3 | 1.16 | 1.08 | 1.03 |
| 1.3 | 1.77 | 1.26 | 1.1 | 1.02 | 0.96 |
| 1.6 | 1.625 | 1.13 | 0.96 | 0.88 | 0.83 |
| 2.0 | 1.5 | 1 | 0.83 | 0.75 | 0.7 |

At present, application of stem-cell technology to tissue engineering is limited by the lack of suitable protocols for inducing SCs differentiation along a differentiation lineage of choice and incorporating SCs into organized complex three-dimensional structures or tissues functional in the vertebrate body. In addition, with restrictions now placed on embryonic tissue use, stem cell research may also be limited by the lack of suitable source tissue from which stem cells can be generated.

As is illustrated in the Examples section which follows, the present inventor has uncovered that micro-organ tissue explants implanted in a host or cultured under suitable conditions can be used as a continuous source of stem cells and that micro-organs or micro-organ conditioned media can be used to induce differentiation of embryonic or adult derived stem cells. In addition, the present inventor has uncovered that acellular scaffold structures generated from micro-organs can be used along with stem cells to generate tissue of a defined function and micro-architecture.

Thus, according to one aspect of the present invention there is provided a method of generating adult stem cells. The method according to this aspect of the present invention is effected by implanting at least one micro-organ explant derived from an adult tissue (e.g., kidney tissue, liver tissue, lung tissue, skin tissue and gut derived tissue) in a mammal (e.g., a pig, a monkey) and isolating cells migrating out of the micro-organ; such cells being adult stem cells.

Implantation is effected in a manner suitable for continuous production and migration of the adult stem cells from the implanted micro-organ. The Examples section which follows provides further description of suitable implantation approaches which can be used with the present methodology.

Isolation of adult stem cells from the mammalian host can be effected using a variety of approaches. For example, the adult stem cells can be harvested from biological fluid (e.g., blood or lymphatic fluid) collected from the host.

Alternatively, adult stem cells can also be generated and isolated by culturing the at least one micro-organ explant in a culture and isolating cells migrating out of the micro-organ.

It will be appreciated that aside from being easy to implement, the present methods are also advantageous in that they provide a continuous source of stem cells, limited only by the time period the micro-organ explants can be kept in culture or implanted.

Further description relating the in-vivo (implanted) or ex-vivo micro-organ culturing methodology utilized by the present invention as well as description relating to adult stem cell recovery and typing are provided in the Examples section which follows.

As is further detailed in the examples section which follows, the adult stem cells recovered by the methods of the present invention are similar in characteristics to embryonic stems cells. These adult stem cells retain pluripotency and are capable of differentiating into a plurality of tissue cell types, depending on the stimuli provided thereto. As such, these cells can be used therapeutically or for research purposes in a manner similar to that proposed for embryonic stem cells.

As is mentioned hereinabove, one major hurdle confronting utilization of stem cells is the lack of protocols for directing differentiation of stem cells into a defined and utilizable tissue.

Thus, according to another aspect of the present invention there is provided a method of inducing stem cells differentiation. The method according to this aspect of the present invention is effected by co-culturing isolated stem cells along with micro-organ(s), or in a micro-organ conditioned medium. As is further illustrated in the Examples section which follows, such culturing stimulates differentiation of adult or embryonic stem cells into a defined tissue type which can be used for a variety of purposes including therapeutic or cosmetic uses.

Although such differentiation can be used to provide differentiated and thus functional cells, in order to generate functional tissue of a defined architecture and organ-like function, the adult stem cells of the present invention as well as embryonic stem cells can be used to seed micro-organ sized scaffolds, thus generating "synthetic" micro-organs.

Such scaffolds can be synthetic polymeric scaffolds which are sized and configured such that when populated with cells, the cells positioned deepest within the scaffold are at least about 100 micrometers and not more than about 225 micrometers away from the cells positioned at a nearest surface formed on the scaffold.

Alternatively, and as described in the Examples section which follows, micro-organ explants can be used to generate an acellular micro-organ derived three dimensional scaffold using, for example, chemical cell-stripping methods.

In any case, such a scaffold when seeded with stem cells (adult or embryonic) and optionally differentiated cells can be used to generate a micro-organ like three dimensional tissue structure. The tissue type and function of such a synthetic micro-organ can be determined by the (i) conditions of culturing; (ii) body tissue type into which the seeded scaffold is implanted; (iii) micro-organ tissue from which the scaffold was generated and/or (iv) type of cells seeded on the scaffold (stem, and/or differentiated cells). In addition, the stem and/or differentiated cells used can be genetically transformed or obtained from transgenic animals to express polypeptides capable of directing tissue differentiation. For example, stem cells can be transformed to express growth factors of the TGF-beta superfamily in order to induce or stimulate differentiation thereof into various cell types.

Depending on their tissue type and purpose, such synthetic micro-organs can be utilized in a manner similar to "natural" micro-organs (see, U.S. Pat. No. 5,888,720, and PCT Applications No. IL00/00365, IL00/00424 and US98/00594 for further detail). It will be appreciated however, that since such synthetic micro-organs can be generated from any cell type of any genetic background, the risk of micro-organ rejection by an individual is virtually non-existent especially in cases where stem cells or self cells are used to seed the scaffold.

Thus, the present invention provides novel approaches for isolating adult stem cells, differentiating such cells as well as embryonic stem cells into various tissue types and using micro-organ derived scaffolds and stem cells for generating synthetic micro-organ structures.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I–III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1–4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I–III Cellis, J. E., ed. (1994); "Culture of Animal Cells—A Manual of Basic Technique" by Freshney, Wiley-Liss, N.Y. (1994), Third Edition; "Current Protocols in Immunology" Volumes I–III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1–317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorpotaed by reference as if fully set forth herein. Other general references are provided throughout this document. The procedures therein are believed to be well known in the art and are provided for the convenience of the reader. All the information contained therein is incorporated herein by reference.

MATERIALS AND EXPERIMENTAL METHODS

Preparation of Micro-Organs

Micro-organs (MOs) were prepared from skin, gut, bone marrow, liver and kidney of a β-galactosidase transgenic mice strain, tg-ROSA (Kennedy and Abkowitz, 1997) as described hereinabove and in U.S. Pat. No. 5,888,720, and PCT Applications No. IL00/00365, IL00/00424 and US98/00594. The use of β-galactosidase transgenic mice allows identification of cells derived therefrom by X-Gal histochemistry staining, of adult normal syngeneic C57 black mice and/or of Sprague Dawley rats. Adult animals were sacrificed by asphyxiation with $CO_2$ and the respective organs removed under sterile conditions. Organs were kept on ice and rinsed once with Ringer solution or DMEM (Beit Haemek, Israel) including 4.5 gr/liter D-glucose and thereafter using a Sorvall tissue chopper, cut into 300 μm slices to form MOs. The MOs were washed again (2–3 times) as above and incubated in DMEM containing 100 units per ml penicillin, 1 mg/ml streptomycin and 2 mM L-glutamine (Beit Haemek, Israel), 5% $CO_2$ atmosphere, 37° C. Incubation medium was change every 1–2 days.

MOs Implantation

Adult C-57 mice were anesthetized using 0.6 mg Sodium Pentobarbital per gram body weight. The mice were shaved, and an incision about 2 cm long was made in the skin at an area above the stomach. A hemostat was used to create a subcutaneous "pocket" at the side of the incision, and 2–6 MOs were implanted inside the pocket. Implantation was done by simply layering the MOs over the muscle layer. The incision was sutured and the animals were kept in a warm, lit room for several hours following which they were transferred to the animal house. Animals were sacrificed at different time interval following implantation and the implanted MOs were dissected from surrounding tissues under a surgical microscope and utilized for β-gal assays, histology and RNA extraction.

Preparation of STO Feeder Layer for Stem Cells (SCs) Growth

Non-dividing mouse STO fibroblast cells were grown in DMEM supplemented with 10% fetal calf serum, 100 units per ml penicillin, 1 mg/ml streptomycin and 2 mM L-glutamine. Medium was changed every day. Prior to use as a feeder layer, STO cells were treated with 0.01 mg/ml mitomycin (Din-Diagnostic) for 3 hours and washed with the same medium.

Isolation and Propagation of Adult Stem Cells (ASCs)

Primary MOs prepared from mouse skin, gut, bone marrow, liver and kidney of the β-galactosidase transgenic mice strain, tg-ROSA (Kennedy and Abkowitz, 1997) were used as a source of adult stem cells (ASCs). Cells derived from this strain can be easily identified by their blue color following X-Gal histochemistry staining. To this end, about 30–100 MOs were plated onto mytomicyn-treated feeder layers of STO cells. MOs were allowed to adhere to the feeder layer and potential ASCs present in the MOs were selected from those cells that migrated out of the MOs and proliferated into colonies on the STO feeder layer. Cells derived from such colonies were replated two to three times on fresh mytomicyn-treated STO feeder layers until they proliferated enough to cover the whole STO feeder layer. After two to three passages, and ascertaining that the amplified cells expressed the β-gal gene, some of the cells were cryopreserved and the remaining cells were tested for their competence and capacity to differentiate in the systems described below.

Isolation and Propagation of Embryonic Stem Cells (ESCs)

Cell culture: CCE ESCs (Levinson-Dushnik and Ben-venisty, 1997) were maintained in Dulbecco's modified Eagle medium (DMEM) supplemented with 15% heat inactivated fetal calf serum (HI-FCS), 100 units per ml penicillin, 1 mg/ml streptomycin, 2 mM L-glutamine, nonessential amino acid solution (Beit Haemek, Israel), 70 μM β-mercaptoethanol and 1,000 units per ml leukemia inhibitory factor (LIF) (Gibco BRL) on mitomycin treated STO cells or on gelatin-coated tissue culture plates. The growth medium was changed every day.

When grown over a non-adhesive plastic, ESCs differentiate and aggregate to form a colony known as embryoid body (EB) (Keller, 1995). At day 3 EBs start to show an outer endodermal layer and inner ectodermal layer (Abe et al., 1996). The EBs used in the experiments described herein were 3 days old. CCE EBs were also grown over non-adhesive plastic petri dish under the same conditions without the addition of LIF; the growth medium was replaced every day.

X-Gal staining: MOs and/or stem cells (SCs) were fixed in a fixation solution containing 0.05 M sodium phosphate buffer (i.e., 0.04 M $Na_2HPO_4$ and 0.011 M $NaH_2PO_4$, pH 7.4), 0.2% gluteraldehyde, 2% formaldehyde and 2 mM $MgCl_2$. Following fixation, the MOs and/or SCs were washed three times with a washing solution containing 0.05 M sodium phosphate buffer, 2 mM $MgCl_2$ and 0.02% NP40. MOs and/or SCs were stained overnight in X-Gal solution (0.05 M sodium phosphate buffer, 5 mM $K_4Fe(CN)_6 3(H_2O)$, 5 mM $K_3Fe(CN)_6$ and 5 μg/ml $C_{14}H_{15}BrClNO_6$ (in dimethyl sulfoxide, DMSO). MOs were further fixed in 4% formaldehyde in phosphate buffered saline (PBS). Thereafter, MOs were covered with TISSUE-TEK O.T.C. Compound (Bel-Gar, Israel) and cryo-sectioned into 8–10 μm thick sections. Some of the sections were further stained with a standard Hematoxylin-Eosin stain Transformation of embryonic stem cells with green fluorescence protein: Isolated ESCs were genetically engineered to constitutively express the green fluorescence protein (GFP). These cells can be identified subsequently by their green fluorescence emission when exited with UV light. To this end, the GFP gene was introduced to CCE ESCs by electroporation. A pEF plink plasmid containing a GFP insert (Tsien R. Y., (1998) Ann. Rev of Biochemistry 67, 509–544) inserted at the NcoI-XbaI cloning sites was linearized by HindIII. ESCs grown as described above were trypsinized and co-transfected with the GFP insert containing plasmid and a $neo^r$ plasmid (Tsien R. Y., (1998) Ann. Rev of Biochemistry 67, 509–544) in a 40:1 ratio. Transfected cells were selected for $neo^r$ by exposure to G418 (250 μg/ml) for two weeks. Two GFP-positive colonies were selected, propagated, cryopreserved and used for further experimentation.

Culture of SCs in MO-conditioned medium: MO-conditioned medium prepared as described above was used to culture SCs. The medium was changed every day.

SCs and MOs mixed cultures: MOs and ESCs or EBs derived cells were co-cultured in CCE ESCs medium (as described herein above) without LIF. Half of the medium was changed every day.

Preparation of "Devitalized" Three-Dimensional Scaffolds from Micro-Organs

MOs are prepared as described previously and are treated for 5 minutes with 0.67% ammonium hydroxide in 0.5% SDS. After all of the cellular mass is removed the remaining extracellular (devitalized acellular) mass is washed thoroughly in five changes of PBS, after which the matrix is ready for use as a three-dimensional scaffold. Either undifferentiated SCs or SCs that have been previously differentiated by any of the methods described above or other methods known in the art are then plated onto the scaffold and cultured for different time periods until the entire matrix is repopulated. SCs alone or in combination with a cell suspension derived from the organ in question can also be plated in order to obtain chimerism and enhance differentiation of the SCs if required.

Monitoring Stem Cell Differentiation

Differentiation of SCs was assessed by transcription of tissue specific genes using RT-PCR.

RNA isolation: Cells were collected from either the culture medium, the culture dish surface or dissected from MOs surface by micropipetting. Total RNA was extracted from tissues or cell with acid-guanidine and phenol using the Chomczynski method (Chomczynski, 1994). RNA was separated on a 1% agarose gel to assess both quantity and quality.

Reverse transcription (RT) PCR: cDNA was synthesized from 1–2 μg total RNA using poly $d(T)_{12-18}$ (Pharmacia Bio-tech) primer and Moloney murine leukemia virus reverse transcriptase (Promega). Two μl cDNA samples were subjected to PCR amplification using Taq DNA polymerase (Promega) in 1.5 mM $MgCl_2$ (37 cycles). The PCR primers used, the fragment sizes and annealing temperatures used for each pair of primers are summarized in Table 2 below:

TABLE 2

| Gene | Primer I, 5'–3' (SEQ ID NO:) | Primer II, 5'–3' (SEQ ID NO:) | Size | $T_m$ |
|---|---|---|---|---|
| β-actin | TACCACAGGCATTGTGATGG (1) | AATAGTGATGACCTGGCCGT (2) | 310 | 55 |
| HNF3β | CGAGCCATCCGACTGGAGC (3) | GACTCGGACTCAGGTGAGGT (4) | 299 | 55 |
| SP-C | ACACCATCGCTACCTTTTCC (5) | CTTTCCTTTACAGACTTCCACC (6) | 435 | 57 |
| CC-10 | TCATGCTGTCCATCTGCTGC (7) | AAAGAGGAAGGAGGGGTTCG (8) | 343 | 55 8 |

TABLE 2-continued

| Gene | Primer I, 5'–3' (SEQ ID NO:) | Primer II, 5'–3' (SEQ ID NO:) | Size | $T_m$ |
|---|---|---|---|---|
| HNF1α | CGAAGATGGTCAAGTCGTAC (9) | GGCAAACCAGTTGTAGACAC (10) | 500 | 55 |
| HNF1β | TTCAGTCAACAGAACCAGGG (11) | CTCTGTGCAATGGCCATGAC (12) | 721 | 55 |
| HNF4 | GATTGACAACCTGCTGCAGG (13) | CCTGCAGCAGGTTGTCAATC (14) | 769 | 55 |
| ζ- glob | GAGAGAGCTATCATCATGTCC (15) | GTCAGGATAGAAGACAGGAT (16) | 394 | 55 |
| CFTR | TCACACTGAGTGGAGGTCA (17) | GGAGTCTTTTGCACAATGGA (18) | 510 | 60 |

PCR products were separated in a 2% agarose gel in the presence of ethidium bromide. Gels were photographed and analyzed densitometrically using the NIH image version.

EXPERIMENTAL RESULTS

Differentiation of embryonic stem cells by co-culturing with micro-organs and by culturing in micro-organs conditioned medium: Four mixed cultures of either ESCs expressing GFP or early (3 days) embryonic bodies (EBs) expressing GFP were co-cultured with liver or lung MOs in standard MOs culture conditions as described above for MOs. In addition, cultures of ESCs expressing GFP or early EBs expressing GFP were cultured in conditioned medium derived from liver or lung MO cultures prepared as described above. Cultures were kept for different time periods and the cells were examined both histologically and for the expression of tissue specific genes. Specifically the expression level of HNF1 (specific to liver), HNF3β (specific to liver), HNF4 (specific to liver), hepatocyte growth factor (HGF),ξ-globin (specific to liver), and cystic fibrosis transmembrane conductance regulator (CFTR) (specific to lung) was monitored via RT-PCR as described hereinabove.

Both ESCs and EB cells (EBCs) attached to the surface of the MOs and remained viable throughout the experiment (typically about a week) (FIG. 1). Furthermore, after 5 to 7 days structural changes were detected both in ESCs and EBCs. In agreement with the histological changes (FIGS. 2a, 2b, FIG. 3), ESCs and EBCs grown in the presence of MOs or MOs conditioned medium showed different gene expression patterns than control undifferentiated cells. Specifically, HNF4 and HGF expression were detected in both ECSs and EBs when cultured together with either liver MOs or liver MOs conditioned medium, ξ-globin expression only in ECs grown together with liver MOs, and CFTR expression only in ESCs supplemented with lung MOs conditioned medium. Taken together, these results clearly indicate that MOs and/or MOs conditioned medium can be used to induce differentiation of ESCs and EBCs to specific cell types.

Micro-Organs (MO) can sustain stem cell growth and differentiation in the absence of native MO cells: As shown in FIGS. 1–3, MOs are capable of directing the differentiation of embryonic stem cells. This differentiating and growth supporting effect of MOs was further demonstrated with transduced, neomycin resistant mouse embryonic stem cells cultured with antibiotic-sensitive mouse lung MOs.

Mouse lung MOs prepared as described above were co-cultured with either neomycin resistant mouse embryoid bodies, or trypsinized embryoid bodies as a cell suspension as described above. The cultures were maintained for 21 days in the presence of 250 µg/ml neomycin, killing all non-resistant cells. When total RNA from the cultures is isolated and separated on agarose gel, the effect of the neomycin is clearly seen: cultures of non-resistant lung MOs alone, without co-cultured stem cells, did not survive, as evidenced by the absence of ethidium bromide staining large and small ribosomal RNA bands (lane 1, FIG. 4). Total RNA from all the surviving co-cultured cells demonstrated viability and neomycin resistance, as indicated by the prominent ribosomal RNA bands (lanes 2–6, FIG. 4). Embryoid body cells co-cultured as single cells (trypsinized Ebs-lanes 5 and 6, FIG. 4)) were as viable as embryonic stem cells (lanes 2–4 (ES), FIG. 4). Embryonic stem cells and embryoid bodies cultured alone retained viability and neomycin resistance (lanes 7 and 8, respectively, FIG. 4).

Micro organs are not only able to support proliferation, but also induce organ-specific differentiation of embryonic stem cells, as demonstrated in FIGS. 1, 2a, 2b and 3. Mouse neomycin-resistant ES and EB cells co-cultured with non-resistant MOs also demonstrated organ-specific gene expression, indicating induction of differentiation in the absence of MO cells. FIG. 5 shows the results of RT-PCR analysis, as described above, of RNA extracted from neomycin-resistant ES and EB cells cultured with (lanes 2–6) and without (lanes 7 and 8, FIG. 5) MOs, as described above. Detection of housekeeping gene (actin) expression (prominent band, lanes 2–8, FIG. 5) in the co-cultured cells, and the lack of gene expression in the MOs exposed to neomycin (absent band, lane 1, FIG. 5) indicate that MO cells are not required for embryoid stem cell proliferation in co-culture. When RNA from the same cultures was analyzed for organ-specific gene expression, using RT-PCR primers detecting lung-specific gene surfactant protein-C (FIG. 6), organ-specific gene transcription was evident in ES and EB cells co-cultured with MOs (lanes 2–6, FIG. 6), while none was detected in the neomycin-sensitive isolated MO culture (lane 1, FIG. 6) or in the resistant ES and EB cells cultured alone (lane 7 and 8, FIG. 6). Thus, the MO, even in the absence of viable cells, is capable of both supporting proliferation and directing accurate organ-specific differentiation of embryoid stem cells.

Adult pluripotent stem cells (AS cells) from mouse micro-organs cultured in developing chick embryos: The above-mentioned experiments clearly show that microorgans can induce proliferation and differentiation of co-cultured embryonic stem cells. However, the ability of microorgans to provide and support the growth of pluripotent stem cells from adult tissues has not been demonstrated. The presence of pluripotent adult stem cells in microorgans derived from mouse epidermis was investigated by implantation of β-galactosidase-positive stem cells isolated from transgenic mouse microorgans in developing chick embryos.

FIG. 7 demonstrates the presence of β-galactosidase expression in transgenic mouse skin-epidermis derived adult stem cells (AS cells) originating from MOs grown on STO feeder layers and exposed to X-gal as described above. Only the transgenic mouse-derived cells stain blue. When these mouse AS cells were injected into developing chick embryos at day 0, the cells could be identified using the X-gal assay. FIG. 8 demonstrates the distribution of the blue-staining AS cells in an early (3 day, stage 18) chick embryo. In this experiment most of the MO-derived skin AS cells were found in the periphery of the developping embryo, and only few cells became incorporated in the embryo In contrast, in a different experiment in which the cells were implanted at the posterior median region of an early gastrula, as shown in FIG. 9, the blue-staining MO derived skin AS cells were found to integrated into the neural plate of neurula stage chick embryos and in FIG. 10 the blue-staining cells were found confined to well-developed mid- and hindbrain structures. Thus, microorgans prepared from adult tissue (in the present case, the epidermis) can provide a source of adult pluripotent stem cells (AS cells), which may be cultured in vitro, implanted and induced to migrate into even non-homologous tissue (in the present case, avian embryos).

Micro-organs can provide an appropriate micro-environment for differentiation of adult pluripotent stem cells: When β-galactosidase transgenic mouse epidermal-derived adult stem (AS) cells are co-cultured with rat lung micro-organs, the resultant tissue specificity is determined by the tissue origin of the MOs. This was demonstrated for embryoid and adult stem cells in the abovementioned examples (see FIGS. 6, and 8–10). Similarly, when β-galactosidase transgenic epidermal-derived adult stem cells were cultured with rat lung micro organs for 10 days, blue-staining AS cells were detected organized as part of distinct alveolar structures, indicating MO-directed integration and differentiation (FIG. 11, and also see below).

Micro-Organs as an in vivo-implanted continuous source of stem cells: Bone marrow micro organs prepared from β-galactosidase transgenic ROSA mice and implanted subcutaneously into syngeneic, β-galactosidase-negative (non-transgenic) mice, as described above, demonstrated growth and tissue specificity characteristic of MO cells, the MO origin of the differentiating stem cells evident from the blue-staining with x-gal (FIG. 12). Surprisingly, the migration of MO derived bone marrow stem cells out of the immediate MO environment, and into the surrounding tissue is indicated by the presence of blue staining cells at a distance from the MO (black arrow, FIG. 12). Thus, when implanted in vivo, MOs constitute a continuous source of stem cells capable of migrating out of the MOs and become incorporated into regenerating tissues at remote locations. This was further demonstrated in partially hepatectomized, syngeneic mice. When five bone-marrow MOs derived from a β-galactosidase transgenic ROSA were implanted on top of a hemostatic matrix near the exposed liver surface and left for ten days, blue-staining transgenic bone marrow micro organ derived cells populate the entire matrix surface (FIG. 17*a*). When the same area was fixed and sectioned, it is apparent that the micro organ derived cells not only cover most of the matrix but have also undergone differentiation, becoming incorporated into part of the newly forming liver sinusoids.

Devitalized micro organ scaffolds support growth and direct differentiation of bone marrow stem cells: Continuous presence of MO cells is not a prerequisite for the proliferation and differentiation of stem cells within MOs. This was demonstrated previously with MO conditioned medium, and in the abovementioned examples, wherein neomycin exposure clearly killed MO cells (FIGS. 4 and 5) but did not inhibit the MO-directed growth and differentiation of co-cultured embryo stem cells and embryoid bodies (FIGS. 4–6). The ability of devitalized, acellular MOs to support growth and differentiation of stem cells is of great importance, both from practical (i.e. clinical) and theoretical considerations.

When micro organs are briefly treated with an ammonium hydroxide-detergent combination as described in the examples section herein, the MO cells are killed and removed with washing. What remains may be described as an organ-specific, three-dimensional scaffold. When β-galactosidase transgenic mouse bone marrow stem cells are plated with devitalized rat liver MO scaffolds (1,000–5,000 cells per MO), incubated for 9 days, fixed and stained with x-gal, the growth and differentiation-promoting effect of the devitalized MO scaffold is discerned. Blue staining mouse β-galactosidase-positive adult stem cells are evident adhering to the devitalized rat liver MO scaffold (FIG. 13).

When similar mouse β-galactosidase transgenic bone marrow cells are plated with rat lung devitalized MO scaffolds (10,000–100,000 cells per MO), and grown for 9 days, induction of characteristic tissue-specific differentiation can be observed. Transverse sections of the cell cultures, fixed and stained with x-gal, reveal blue-staining mouse adult stem cells adhering to the devitalized scaffold and preservation of lung alveolar structure, despite the mouse bone marrow (blue staining) origin of the cells (FIGS. 14 and 15). Thus, devitalized MO scaffolds are capable of supporting the growth, inducing and maintaining tissue specific morphological differentiation of species- and tissue non-related adult stem cells.

Micro organ direction of stem cell differentiation, despite the absence of viable cells, was further demonstrated by RT-PCR analysis of lung-specific gene expression in mouse adult bone marrow stem cells cultured 9 days with devitalized rat lung MO scaffolds. Total RNA extracted, as described in the examples section above, from MO scaffolds and from mouse bone marrow stem cells growing and differentiated in devitalized rat lung MO scaffolds (FIGS. 14 and 15) was analyzed by RT-PCR for expression of CC-10, a clara cell lung specific gene. No lung-specific gene expression is noted in the devitalized MO scaffolds alone (lanes 2 and 3, FIG. 16), confirming the efficient devitalization of the MOs by treatment with the amonia solution?. In a number, but not all, of the mouse bone marrow adult stem cells cultured with MO scaffolds, clear evidence of lung-specific CC-10 expression in the RNA is seen (lanes 7 and 18, FIG. 16).

Taken together, these results demonstrate the ability of micro organs to support the growth and proliferation of embryonic and adult derived stem cells, of homologous and non-homologous tissue and species origin. Furthermore, experiments with neomycin non-resistant MOs, and devitalized MO scaffolds unexpectedly demonstrated MO-directed growth and differentiation of non-homologous adult and embryo-derived stem cells in the absence of viable MO cells, of significant importance for both clinical and research applications. Of even greater potential importance is the demonstration that MOs may be a source of adult pluripotent stem cells (AS) and, when transplanted into host animals, will provide differentiating stem cells sensitive to ambient tissue-specific differentiation signaling, which are capable of migrating out of the MOs to remote tissue locations.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES

1. Keller G. M. (1995) In vitro differentiation of embryonic stem cells. Curr-Opin-Cell-Biol 7, 862–869.
2. O'Shea K. S (1999) Embryonic stem cell models of development. Anat-Record 257, 32–41.
3. Rudnicki M. A., and McBurney M. W. (1987) Cell culture methods and induction of differentiation of embryonic carcinoma cell linSC, p. 19–49 in Robertson (ed.),
4. Chomczynski, P. (1994) Teratocarcinoma and embryonic stem cells: a practical approach, 1$^{st}$ ed. IRL prSCs, Washington D.C., Cell biology: a laboratory handbook, ed. E, C. J.(Academic press, Vol. 1, pp. 680–683.
5. Kennedy D W, Abkowitz J L (1997) Kinetics of central nervous system microglial and macrophage engrafment: analysis using a transgenic bone marrow transplantation model. Blood 90(3), 986–993
6. Abe K., Niwa H., Iwase K., Takiguchi M., Mori M., Abe S. I., Abe K., and Yamamura K. I. (1996). Endoderm-Specific gene expression in embryonic stem cells differenetiated to embryoid bodies. Expr-Cell-Res 229, 27–34.
7. Levinson-Dushnik M., and Benvenisty N. (1997). Involvement of Hepatocyte nuclear factor 3 in endoderm differentiation of embryonic stem cells. Mol-Cell-Biol 17(7),3817–3822.
8. Mezey E, Chandross K J, Harta G, Maki R A, McKercher S R. cells bearing neuronal antigens generated in vivo from bone marrow. Science. Dec. 1, 2000;290(5497): 1779–82.
9. Bjornson C R, Rietze R L, Reynolds B A, Magli M C, Vescovi A L. a hematopoietic fate adopted by adult neural stem cells in vivo. Science. Jan. 22, 1999;283(5401): 534–7.
10. Kocher et al (2001) Nature medicine April 2001
11. Orlic et al 2001. Nature April 2001.

What is claimed is:

1. A method of generating an artificial micro-organ comprising:
   (a) providing devitalized, acellular, tissue-derived three dimensional scaffold, said acellular three dimensional scaffold being of dimensions selected such that when populated with cells, said cells positionable deepest within said scaffold are at least about 100 micrometers and not more than about 225 micrometers away from said cells positioned at a nearest surface exposed to a source of gas and nutrients formed on said scaffold; and
   (b) seeding said acellular three dimensional scaffold with stem cells, progenitor cells or differentiated cells, wherein said differentiated cells are of the same tissue from which the scaffold was generated, and
   (c) providing conditions for cell growth and proliferation.

2. The method of claim 1, wherein said stem cells are adult stem cells.

3. The method of claim 1, wherein said stem cells are embryonic stem cells.

4. The method of claim 1, wherein said cells seeded on said acellular three dimensional scaffold are a mixed population of cells including stem cells, progenitor cells and differentiated cells, wherein said differentiated cells are of the same tissue from which the scaffold was generated.

5. The method of claim 1, wherein said cells seeded on said acellular three dimensional scaffold are genetically transformed to express at least one exogenous polypeptide.

6. The method of claim 1, wherein said stem cells are genetically transformed to express at least one exogenous polypeptide.

7. The method of claim 1, further comprising the step of generating said acellular three dimensional scaffold from a tissue-derived micro-organ.

8. The method of claim 7, wherein said step of generating is effected by subjecting said tissue-derived micro-organ to conditions selected suitable for removing cells and not acellular matrix from said micro-organ.

9. The method of claim 7, wherein said micro-organ is derived from an adult tissue of a type selected from the group consisting of skin, lung, kidney, liver and bone marrow.

10. The method of claim 7, wherein said progenitor cells are progenitor cells derived from the same tissue source as said micro-organ.

* * * * *